United States Patent
Wu et al.

(10) Patent No.: US 12,214,101 B2
(45) Date of Patent: Feb. 4, 2025

(54) PRE-SATURATED DISINFECTING DISPOSABLE MICROFIBER WIPES

(71) Applicant: Rubbermaid Commercial Products LLC, Atlanta, GA (US)

(72) Inventors: Weidong Wu, Charlotte, NC (US); Brian Smallwood, Huntersville, NC (US); Dimple Bhesania, Concord, NC (US); Dan Troutman, Palm Beach Gardens, FL (US)

(73) Assignee: Rubbermaid Commercial Products LLC, Atlanta, GA (US)

( * ) Notice: Subject to any disclaimer, the term of this patent is extended or adjusted under 35 U.S.C. 154(b) by 0 days.

(21) Appl. No.: 18/452,111

(22) Filed: Aug. 18, 2023

(65) Prior Publication Data
US 2023/0390445 A1    Dec. 7, 2023

Related U.S. Application Data

(63) Continuation of application No. 17/937,755, filed on Oct. 3, 2022, now Pat. No. 11,771,790.
(Continued)

(51) Int. Cl.
*B08B 1/14* (2024.01)
*A61L 2/18* (2006.01)
(Continued)

(52) U.S. Cl.
CPC .................. *A61L 2/26* (2013.01); *A61L 2/18* (2013.01); *B08B 1/143* (2024.01); *D05B 93/00* (2013.01);
(Continued)

(58) Field of Classification Search
CPC ........... B08B 1/006; A47L 13/17; A47L 13/16
See application file for complete search history.

(56) References Cited

U.S. PATENT DOCUMENTS 7,670,967 B2    3/2010 Runge et al.
7,838,447 B2    11/2010 Clark et al.
(Continued)

FOREIGN PATENT DOCUMENTS

JP    2010275680 A    * 12/2010
JP    3233906 U    * 9/2021
(Continued)

OTHER PUBLICATIONS

PDI, "Sani-Cloth® AF3 Germicidal Disposable Wipe" https://pdihc.com/products/environment-of-care/sani-cloth-af3-germicidal-disposable-wipe/; accessed Sep. 6, 2022, 1 page.
(Continued)

*Primary Examiner* — Shay Karls
(74) *Attorney, Agent, or Firm* — Eversheds Sutherland (US) LLP

(57) ABSTRACT

A pre-saturated disposable disinfecting wipe may include a microfiber cloth. The microfiber cloth may include a low weight substrate having a first face and an opposed second face, and microfiber yarn attached to the low weight substrate in a plurality of parallel rows of stitches. The pre-saturated disposable disinfecting wipe further includes a disinfecting formulation saturated in the microfiber cloth. The pre-saturated disposable disinfecting wipe may have a single-touch two-minute wetness coverage of more than 100 in². A method of manufacturing a pre-saturated disposable disinfecting wipe may include saturating, with a disinfecting formulation, a microfiber cloth.

22 Claims, 3 Drawing Sheets

Related U.S. Application Data

(60) Provisional application No. 63/253,815, filed on Oct. 8, 2021.

(51) Int. Cl.
    *A61L 2/26*       (2006.01)
    *D05B 93/00*     (2006.01)
    *A61L 101/18*    (2006.01)

(52) U.S. Cl.
    CPC ....... *A61L 2101/18* (2020.08); *D10B 2331/04* (2013.01); *D10B 2401/02* (2013.01); *D10B 2401/063* (2013.01); *D10B 2503/00* (2013.01)

(56) References Cited

U.S. PATENT DOCUMENTS

| | | |
|---|---|---|
| 8,282,776 B2 | 10/2012 | Smith et al. |
| 8,318,654 B2 | 11/2012 | Hoffman et al. |
| 8,328,988 B2 | 12/2012 | Champion et al. |
| 8,563,017 B2 | 10/2013 | Cunningham et al. |
| 8,603,297 B2 | 12/2013 | Zwick et al. |
| 8,927,480 B2 | 1/2015 | Williams et al. |
| 9,089,138 B2 | 7/2015 | Higgins et al. |
| 9,096,821 B1 | 8/2015 | Hope et al. |
| 9,655,491 B2 | 5/2017 | Sumnicht et al. |
| 9,826,736 B2 | 11/2017 | Napolitano et al. |
| 10,136,790 B2 | 11/2018 | Wildeman et al. |
| 10,196,780 B2 | 2/2019 | Lee et al. |
| 10,351,998 B2 | 7/2019 | Baer et al. |
| 10,555,521 B2 | 2/2020 | Joshi |
| 10,568,321 B2 | 2/2020 | Bentley et al. |
| 10,822,576 B2 | 11/2020 | Mitchell et al. |
| 10,982,177 B2 | 4/2021 | Dani |
| 2007/0012846 A1* | 1/2007 | Wan ............... A47K 10/185 248/905 |
| 2010/0147203 A1* | 6/2010 | MacDonald ......... A47L 13/17 112/475.18 |
| 2011/0146017 A1* | 6/2011 | Wildeman ........... A47L 13/17 112/475.08 |
| 2012/0207652 A1* | 8/2012 | Wildeman ............. A61L 2/18 422/292 |
| 2014/0171512 A1 | 6/2014 | Kloeppel et al. |
| 2015/0330029 A1 | 11/2015 | Cordero et al. |
| 2018/0084777 A1 | 3/2018 | Jiang |
| 2018/0343859 A1 | 12/2018 | Jiang et al. |
| 2019/0053493 A1 | 2/2019 | Jiang et al. |
| 2020/0080031 A1 | 3/2020 | Dani et al. |
| 2020/0198303 A1 | 6/2020 | Dani et al. |
| 2020/0288708 A1 | 9/2020 | Chan et al. |
| 2020/0305435 A1 | 10/2020 | McGeechan et al. |
| 2020/0354651 A1 | 11/2020 | Tollens et al. |
| 2021/0163854 A1 | 6/2021 | Tollens et al. |
| 2021/0369075 A1 | 12/2021 | Wu |

FOREIGN PATENT DOCUMENTS

| | | | |
|---|---|---|---|
| KR | 101907688 B1 * | 10/2018 | |
| WO | 2021089388 A1 | 5/2021 | |

OTHER PUBLICATIONS

PDI, "Super Sani-Cloth® Germicidal Disposable Wipe" https://pdihc.com/products/environment-of-care/super-sani-cloth-germicidal-disposable-wipe/, accessed Sep. 6, 2022, 1 page.

Diversey, "Oxivir® Tb Wipes" https://diversey.com/en/product-catalogue/oxivir-tb-wipes-4599516-nam; accessed Sep. 6, 2022, 1 page.

Clorox, "Clorox Healthcare® Bleach Germicidal Disinfectants" https://www.cloroxpro.com/products/clorox-healthcare/bleach-germicidal-disinfectants/; accessed Sep. 6, 2022, 1 page.

Numed Healthcare "Clinell Universal Wipes (Pack of 200)" https://www.numed.co.uk/products/clinell-universal-wipes-pack-of-200; accessed Sep. 6, 2022, 1 page.

* cited by examiner

PRE-SATURATED DISINFECTING DISPOSABLE MICROFIBER WIPES

CROSS-REFERENCE TO RELATED APPLICATIONS

This application is a continuation of U.S. patent application Ser. No. 17/937,755, filed on Oct. 3, 2022, which claims the benefit of U.S. Provisional Application No. 63/253,815, filed on Oct. 8, 2021, which are both incorporated herein by reference.

TECHNICAL FIELD

The present disclosure generally relates to disposable disinfecting wipes and methods for manufacturing the same.

BACKGROUND

Disposable disinfecting wipe products have recently gained popularity. Such wipe products typically incorporate a nonwoven substrate that is saturated after purchase with a cleaning or sanitizing solution, typically having to soak the cloths in the solution for an extended period. Flat or textured nonwoven substrate have been used successfully, but such nonwoven substrate must have a substantial weight to avoid falling apart during use.

Thus, it would be desirable to provide improved disposable disinfecting wipes.

SUMMARY

The present disclosure generally relates to disposable disinfecting cloths, also referred to interchangeably as wipes throughout the present disclosure, and methods for manufacturing the same. More specifically, the present disclosure relates to pre-saturated disposable disinfecting microfiber cloths having a relatively low weight substrate with microfiber yarns associated therewith.

In embodiments, the present disclosure describes a pre-saturated disposable disinfecting wipe. The pre-saturated disposable disinfecting wipe includes a microfiber cloth. The microfiber cloth may include a low weight substrate having a first face and an opposed second face, and microfiber yarn attached to the low weight substrate in a plurality of parallel rows of stitches. The pre-saturated disposable disinfecting wipe further includes a disinfecting formulation saturated in the microfiber cloth. The pre-saturated disposable disinfecting wipe may have a single-touch two-minute wetness coverage of more than 100 $in^2$.

In embodiments, the present disclosure describes a method of manufacturing a pre-saturated disposable disinfecting wipe. The method may include providing a low weight substrate having a first face and an opposed second face. The method may further include attaching a microfiber yarn to the low weight substrate in a plurality of parallel rows of stitches. The method may further include saturating the microfiber cloth with a disinfecting formulation. The pre-saturated disposable disinfecting wipe may have a single-touch two-minute wetness coverage of more than 100 $in^2$.

In embodiments, the present disclosure describes a method of manufacturing a pre-saturated disposable disinfecting wipe. The method may include saturating, with a disinfecting formulation, a microfiber cloth. The microfiber cloth may include a low weight substrate having a first face and an opposed second face, and microfiber yarn attached to the low weight substrate in a plurality of parallel rows of stitches. The pre-saturated disposable disinfecting wipe may have a single-touch two-minute wetness coverage of more than 100 $in^2$.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout the present disclosure, depending on the context, singular and plural terminology may be used interchangeably.

Figure 1:
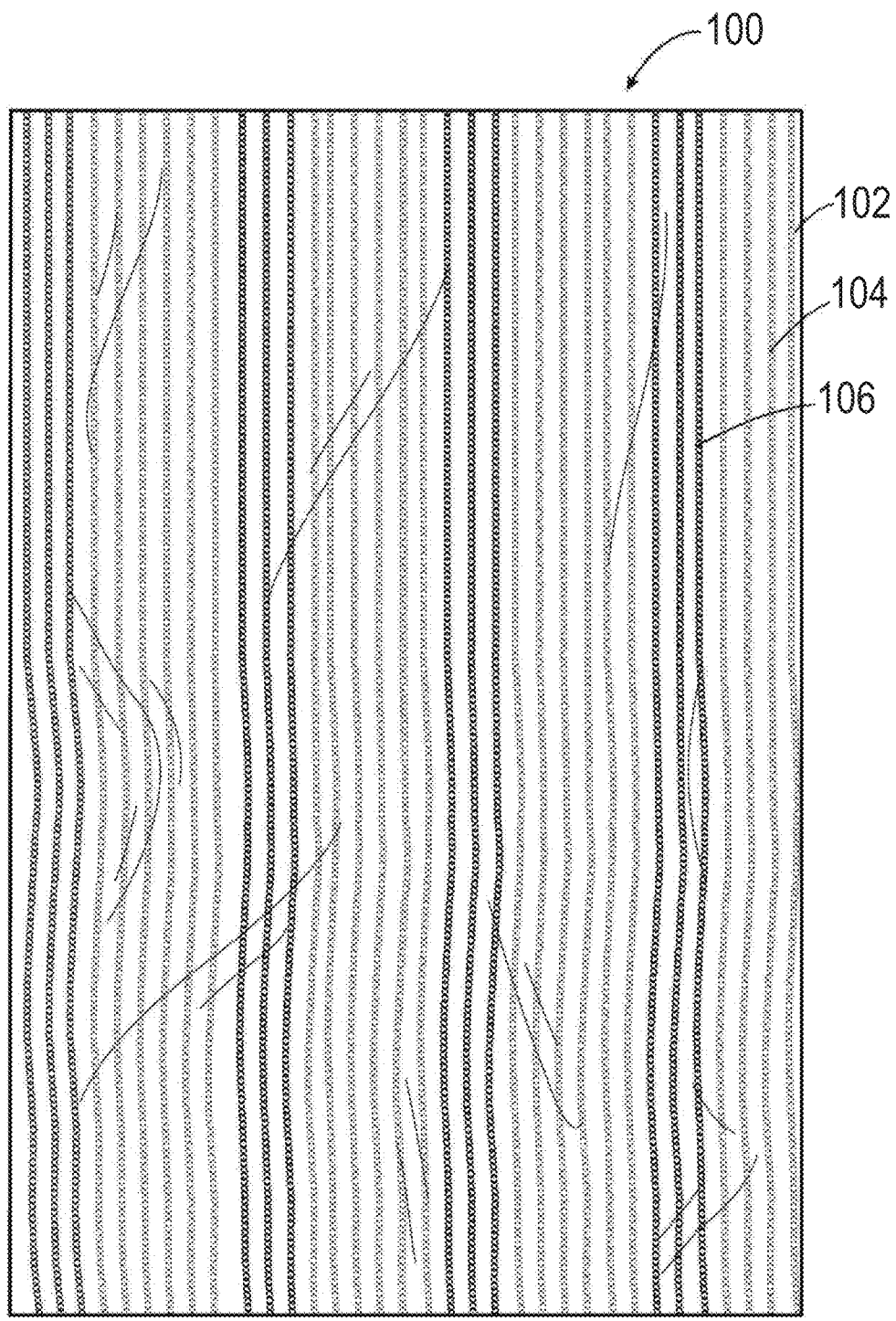
FIG. 1 illustrates a top view of a disposable cleaning cloth including a substrate and a microfiber yarn.

The present disclosure will now provide a more detailed and specific description that will refer to the accompanying drawings. The drawings and specific descriptions of the drawings, as well as any specific or other embodiments discussed, are intended to be read in conjunction with the entirety of the present disclosure

DETAILED DESCRIPTION

The present disclosure generally relates to disposable disinfecting cloths, also referred to interchangeably as wipes throughout the present disclosure, and methods for manufacturing the same. As used herein, "microfiber cloths" may refer to any suitable configuration of a microfiber cloth having a substrate with associated microfiber yarn stitches. For example, suitable microfiber cleaning cloths may be manufactured via sewn stitches, such as is disclosed in U.S. application Ser. No. 17/331,060, filed May 26, 2021, the disclosure of which is incorporated by reference in its entirety. For example, suitable microfiber cleaning cloths may be manufactured by stitch-bonding, such as disclosed in U.S. Pat. No. 9,049,974, filed Oct. 17, 2014, the disclosure of which is incorporated by reference in its entirety. Disinfecting solution may be applied to microfiber cloths, with the microfiber cloths providing improved cleaning and strength properties compared to conventional cotton or other cloths, and the disinfection solution providing disinfection.

The pre-saturated disposable disinfecting wipes include a microfiber cloth formed of a low weight substrate having a first face and an opposed second face, with a microfiber yarn associated with the low weight substrate in a plurality of parallel rows of stitches, and a disinfecting formulation saturated into the microfiber cloth. Such wipes with microfiber cloth including microfiber yarn may provide enhanced impregnation and retention of disinfecting fluid, while also facilitate sufficient release for providing wetting characteristics. For example, a pre-saturated disposable disinfecting wipe may have a single-touch two-minute wetness coverage of more than 100 $in^2$.

The present disclosure includes non-limiting embodiments of pre-saturated disposable disinfecting wipe and methods for manufacturing the same. The embodiments are described in detail herein to enable one of ordinary skill in the art to practice the pre-saturated disposable disinfecting cloths and associated methods of making, although it is to be understood that other embodiments may be utilized and that logical changes may be made without departing from the scope of the disclosure. Throughout the disclosure, depending on the context, singular and plural terminology may be used interchangeably.

The pre-saturated disposable disinfecting wipes described herein utilize a low weight substrate material compared to commercially available textures and flat nonwoven wipes. A microfiber yarn is associated with the low weight substrate in parallel rows of straight stitches, in a pattern and amount effective to provide additional structural stability to the cloth. In certain embodiments, the yarn stitches also provide a textured surface to aid in cleaning effectiveness of debris particles, for both consumer and commercial cleaning applications. It has been found that the microfiber yarn stitches also help absorb the disinfecting formulation. Thus, the pre-saturated disposable disinfecting wipes described herein may be relatively lightweight, while providing superior wipe strength, disinfecting ability, liquid release ability, absorption ability, and cleaning ability in a disposable format. Thus, these pre-saturated disposable disinfecting wipes may provide a satisfactory level of cleaning performance for a disposable wipe (e.g., disinfecting larger surfaces with each wipe), while being formed of lightweight, disposable materials.

The pre-saturated disposable disinfecting wipes described herein also may provide good dust and particle trapping, 99.7% microorganism removal, or 99.86% removal for *staphylococcus, pseudomonas*, and *C. diff*, without substantially binding molecules in the disinfectant formulation, higher abrasion and tear resistance, and clean larger surfaces than other pre-saturated disposable disinfecting wipes. The pre-saturated disposable disinfecting microfiber wipes described herein are more effective at cleaning compared to other pre-saturated disposable disinfecting wipes.

Disinfecting formulations used to pre-saturate the wipes described herein may contain alcohol, quaternary ammonium chloride (QUAT), quaternary ammonium chloride (QUAT) and alcohol, chlorine bleach, citric acid, peroxygens such as hydrogen peroxide, and peracetic acid. Particularly, it has been found that QUAT and chlorine bleach may chemically bind in lower quantities to the microfiber cloths described herein than to other types of disposable wipes.

Particularly in healthcare environments, such as hospitals, quaternary ammonium chlorides are frequently used with mops and wipes as disinfectants. However, these disinfectants are often absorbed by or bound to split bi-component microfibers, such as those contained in microfiber mops and cleaning wipes, when the microfibers are immersed in disinfectant solutions during cleaning, thereby reducing the concentration of any quaternary ammonium chloride-based disinfectant used with these microfibers, and reducing the killing effectiveness of the quaternary ammonium chloride-based disinfectant solution.

In some embodiments described herein, the pre-saturated disposable disinfecting wipe may not substantially chemically bind QUAT or chlorine bleach. For example, in some embodiments, the microfiber cloth, when pre-saturated in a formulation containing QUAT or chlorine bleach and subsequently removed from the formulation, does not substantially alter the concentration of the QUAT or chlorine bleach. As used herein, a wipe that does not substantially alter the concentration of the QUAT or chlorine bleach refers to a wipe that does not preferentially bind the QUAT or chlorine bleach, or to a wipe that is QUAT and chlorine bleach safe and compatible. That is, the concentration of any QUAT or chlorine bleach disinfectant formulation used with the wipe does not substantially differ over time from the initial concentration of the liquid formulation. For example, in some embodiments, the concentration of QUAT or chlorine bleach formulation absorbed by the cloth differs by less than 5% from the concentration of any remaining formulation in 8 hours.

Various embodiments of pre-saturated disposable disinfecting wipes and methods for manufacture of the same are described below.

In embodiments, a pre-saturated disposable disinfecting wipe is provided. As shown in FIG. 1, the disposable cleaning cloth 100 that is saturated with disinfecting formulation includes a low weight substrate 102, which has a first face and an opposed second face, and a microfiber yarn 104 associated with the low weight substrate 102 in a plurality of parallel rows of stitches. The microfiber yarn may be associated with the low weight substrate in any suitable configuration to provide the desired cleaning and absorbency properties.

In embodiments, the microfiber yarn is sewn to the low weight substrate in a plurality of parallel rows of straight stitches, such that the straight stitches are substantially flush with the first and second faces of the substrate 102. As used herein, the phrase "substantially flush with the first and second faces of the substrate" refers to the straight stitches lying flat or level along the respective surfaces of the substrate, such that no visible gap is present between the face and the stitch when the cloth is laid flat at rest. For example, the substantially flush straight stitches are not looped or otherwise stitched to form a gap between the yarn and the substrate. It has been discovered that the substantially flush straight stitches described herein provide a strong cleaning performance, including good dust and particle trapping, despite lying flush with the surface. These features also allow absorption of a disinfecting formulation into the cloth.

In another embodiment, the microfiber yarn is associated with the substrate using a stitch-bond method to form an arrangement of texture-imparting ridges on the surface of the wipe. The stitch-bond system may use alternating rows microfiber 204 and an optional fiber yarn 206, as described in more detail below.

The microfiber cloth may be any suitable microfiber cloth as described herein, and may have a weight of 150 g/m$^2$ or less, such as 75 g/m$^2$ or less. In certain embodiments, the microfiber cloth has a weight of about 10 g/m$^2$ to about 150 g/m$^2$, such as about 30 g/m$^2$ to about 65 g/m$^2$, such as about 45 g/m$^2$ to about 65 g/m$^2$. As used herein, the term "about" when used with reference to a numerical value, refers to an amount that is plus or minus up to 3 percent of the stated numerical value.

In embodiments, the substrate may have a paper or fabric construction. The paper or fabric construction may display suitable fluid absorbency and release properties. For example, the low weight substrate may have an absorbency of from about 300% to about 800% its weight. Specifically, a disinfecting formula may be saturated in the microfiber cloth between an amount of about 350% (or 3.5 times) to about 650% (or 6.5 times) the dry weight of the microfiber cloth. A disinfecting formula may be saturated in the microfiber cloth in an amount of about 350% (or 3.5 times) to about 450% (or 4.5 times) the dry weight of the microfiber cloth for a 55 g/m$^2$ to 70 g/m$^2$ microfiber cloth.

For example, the low weight substrate may be a cotton cellulose or rayon cellulose paper. In other embodiments, the low weight substrate is a nonwoven fabric. For example, the nonwoven fabric may be formed of suitable materials, such as polyester, polypropylene, nylon, acrylic, cotton, rayon, and blends of any of these materials. For example, the nonwoven fabric may be formed via suitable nonwoven fabrication methods, such as spun-bonding, needle-punching, and hydro-entanglement. In one embodiment, the low weight substrate is a needle-punched nonwoven polyester configuration.

In embodiments, the disposable disinfecting cloths may include a single nonwoven fabric or paper layer forming the low weight substrate. In other embodiments, the low weight substrate may be formed of multiple layers.

The microfiber yarn may be formed of suitable microfibers in any suitable configuration. For example, the microfibers may be sized with a relatively small diameter and deliver good water absorbency. For example, the microfibers may have a size of about 0.36 to about 1 denier, such as about 0.52 denier. The microfibers may be formed of suitable materials, such as polyesters, polypropylene, nylon, and blends of any of these materials.

A microfiber yarn is formed of a plurality of microfibers, i.e., microfiber filaments. For example, the microfiber yarn may be formed of from about 50 to about 350 microfiber filaments, such as from about 75 to about 300 filaments, or such as from 100 to 200 filaments. In certain embodiments, the microfiber yarn has a denier of from about 50 to about 200, such as from 50 to 100 denier, such as from 65 to 85 denier.

Figure 2:
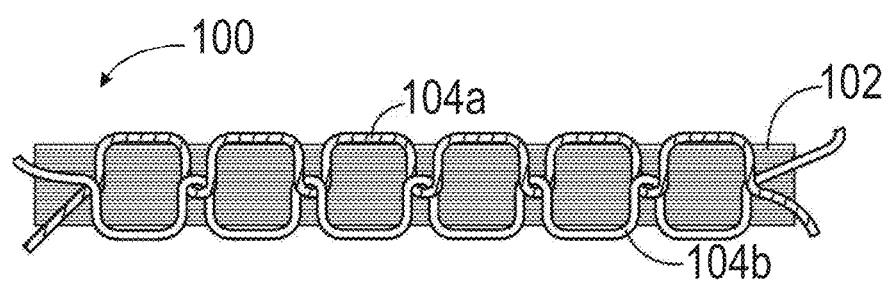
FIG. 2 illustrates a cross-section of a single row of straight stitches of the microfiber yarn in the substrate of the disposable cleaning cloth of FIG. 1.

FIG. 2 illustrates a cross-section of a single row of straight stitches of yarn 104 in the substrate 102 of a disposable cleaning cloth 100 that is saturated with disinfecting formulation. As shown, in certain embodiments of the yarn, the straight stitch yarn pattern is formed by an upper yarn 104*a* and a lower yarn 104*b*. The upper yarn 104*a* is sewn along the first, upper surface of the substrate 102, while the lower yarn 104*b* is sewn along the opposed, lower surface of the substrate 102. Such straight stitch patterns are formed by standard sewing machines. As described herein, both the upper and lower yarns may be a microfiber yarn. In certain embodiments, the upper and lower yarns are identical. In other embodiments, the upper and lower yarns are different microfiber yarns. For example, the upper and lower yarns may have different denier or different material.

As described herein, the microfiber yarn 104 is associated with the substrate 102 in a plurality of parallel rows of stitches. For example, the parallel rows may be straight lines, or other patterns, such as serpentine or zig-zag shaped. For example, the parallel rows may be substantially continuous over the width and length of the disinfecting cloth. The stitches may be provided in a suitable stitch density per area to provide the desired strength reinforcement to the substrate and to provide the desired cleaning performance. For example, the parallel rows of stitches may be spaced from one another by about 0.5 mm to about 5 mm, such as from about 1 mm to about 3 mm. In certain embodiments, the straight stitches of the microfiber yarn are present in an amount of about 50 to about 500 stitches per square inch, such as about 100 to about 300 stitches per square inch, such as from 150 to about 250 stitches per square inch, or about 150 to about 200 stitches per square inch, such as about 180 or 200 stitches per square inch.

In certain embodiments, as shown in FIG. 1, a disinfecting cloth 100 further includes an optional fiber yarn 106 sewn to the low weight substrate 102 in a plurality of parallel rows of straight stitches, such that the straight stitches are substantially flush with the first and second faces of the substrate, the fiber yarn stitches being substantially parallel to the microfiber yarn 104 stitches. For example, the optional fiber yarn may not be a microfiber yarn, but may be a yarn formed of larger filaments, such as filaments having a size of greater than 1 denier. In certain embodiments, one, two, three or more of the fiber yarns are provided between sets of parallel rows of straight microfiber yarn stitches (e.g., sets of two, three, four, five, six, seven, eight, nine, ten or more rows). For example, the interspersed fiber yarns 106 may provide enhanced strength and stiffness for the disinfecting cloth.

Figure 3:
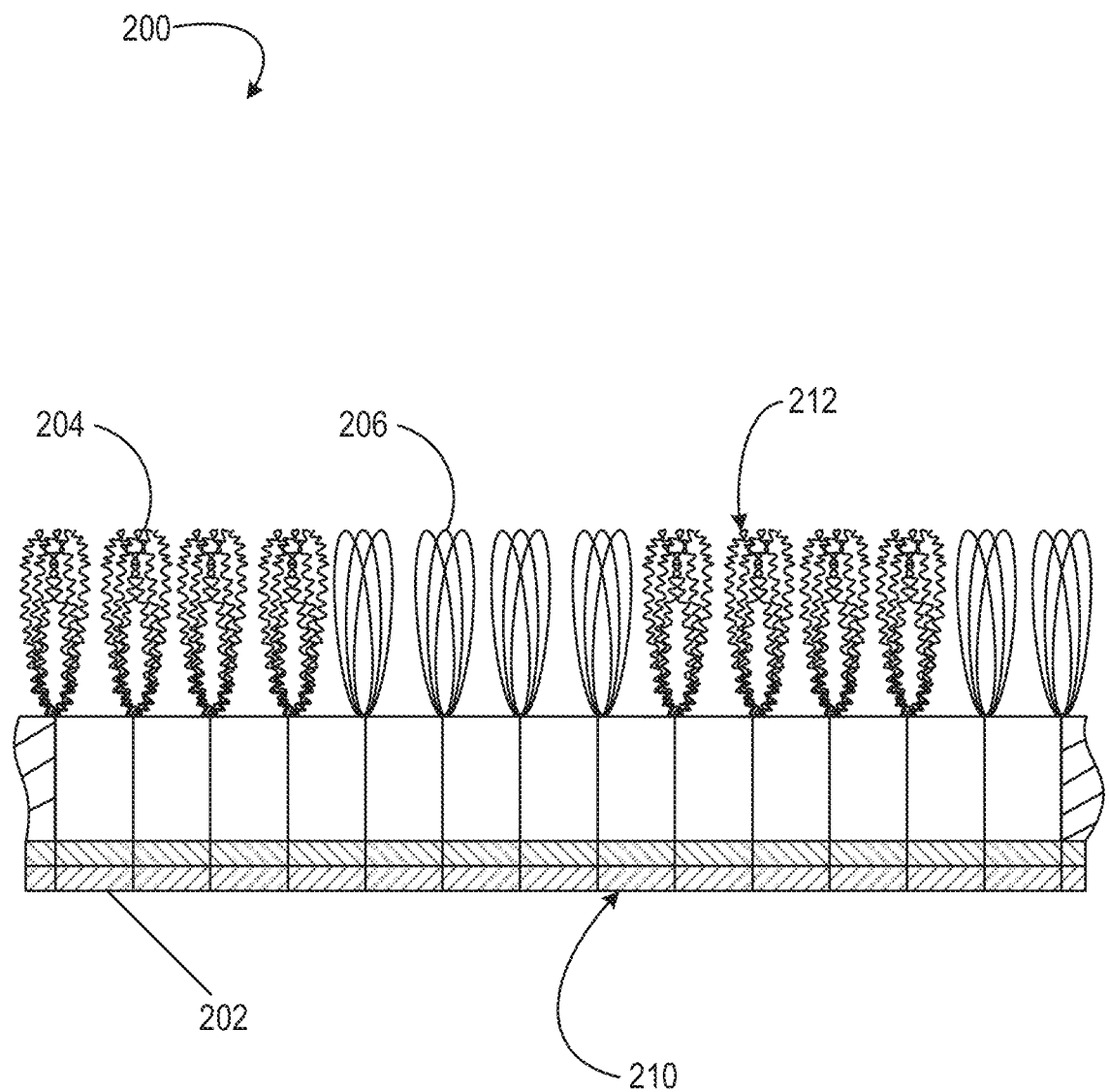
FIG. 3 illustrates a cross-section of a single row of straight stitches of a microfiber yarn associated with a substrate in a stitch-bond configuration.

In certain embodiments, as shown in FIG. 3, the disposable cleaning cloth 200 that is saturated with disinfecting formulation includes a low weight substrate 202, which has a first face and an opposed second face, and a microfiber yarn 204 associated with the low weight substrate 202 in a plurality of parallel rows of stitches. The microfiber yarn is associated with the substrate in FIG. 3 in a "stitch-bond" configuration.

In certain embodiments, as shown in FIG. 3, a disinfecting cloth 200 further includes an optional fiber yarn 206 sewn to the low weight substrate 202 in a plurality of parallel rows of stitches. Both the optional fiber yarn 206 and the microfiber yarn 204 together comprise surface loops 212 and flat locking stitches 210. The surface loops 212 may define a "cleaning face" of the wipe while the flat locking stitches 210 may form a back surface of the substrate 202 that can attach to other cleaning instruments, such as a mop or cleaning pad handle.

The disposable disinfecting cloth is pre-saturated with a disinfecting formulation. The disinfecting formulation can be any suitable disinfecting formulation, including but not limited to formulations containing alcohol, quaternary ammonium chloride (QUAT), quaternary ammonium chloride (QUAT)/alcohol, chlorine bleach, citric acid, peroxide-based formulas such as hydrogen peroxide, and peracetic acid. It has been discovered that the disinfecting formulations saturated in the microfiber cloth makes the wipe effective to clean a relatively large surface area as well as keep the cleaned surface wet for a longer time.

Methods of making a pre-saturated disposable disinfecting wipe 100 are provided. These methods may be used to make microfiber wipes having any of the features, or any combination of the features, described herein. In one embodiment, a method includes providing a low weight substrate 102 having a first face and an opposed second face, and associating a microfiber yarn 104 with the low weight substrate 102 in a plurality of parallel rows of stitches.

As described above, the microfiber yarn may be sewn to the low weight substrate in a plurality of parallel rows of straight stitches, such that the straight stitches are substantially flush with the first and second faces of the substrate 102. In certain embodiments, the sewing is performed on a multiline sewing machine.

As described above, the microfiber yarn may be stitch-bonded to the low weight substrate in a plurality of parallel rows of straight stitches, such that the stitches define loops 212 extending from at least one face of the substrate and flat locking stitches 210 on the other surface or inside of the substrate.

In certain embodiments, the method also includes associating an optional fiber yarn 106 with the low weight substrate 102 in a plurality of parallel rows of stitches. For example, the optional fiber yarn may be associated with the substrate in the same manner as the microfiber yarn. In certain embodiments, the fiber yarn stitches are substantially parallel to the microfiber yarn stitches. In other embodiments, the fiber yarn stitches 206 form further loops 212 on one surface of the substrate 202 and flat locking stitches 210 on the other surface of the substrate 202.

In certain embodiments, the disposable microfiber cloth 100, 200 is then saturated with disinfecting formulation. This disinfecting formulation may contain alcohol, quaternary ammonium chloride, quaternary ammonium chloride (QUAT) and alcohol, chlorine bleach, citric acid, peroxide-based chemicals such as hydrogen peroxide, or peracetic acid. The disinfecting formulation may be saturated in an amount between about 3 times and 8 times the dry weight of the microfiber cloth, such as from about 350% (or 3.5 times) to about 650% (or 6.5 times) the dry weight of the microfiber cloth. For example, a disinfecting formula may be saturated in the microfiber cloth in an amount of about 350% (or 3.5 times) to about 450% (or 4.5 times) the dry weight of the microfiber cloth for a 55 g/m$^2$ to 70 g/m$^2$ microfiber cloth.

had a denier of 75. Surface coverage tests were performed to compare the experimental microfiber wipes with the commercially available nonwoven wipes. Desired contact time and time to kill for microbes vary depending on a number of factors, including type of microbe, type of disinfecting formulation, liquid release, etc. For the wipe to achieve the desired contact time, it must keep the surface completely wet for the requisite time.

TABLE 1 illustrates the results of the surface coverage test for the pre-saturated disposable disinfecting microfiber cloth as compared to traditional pre-saturated nonwoven disposable cloths. "Surface area (in$^2$) w/ multiple touches" is the total surface area in square inches that one wipe was able to keep completely wet during a 2 minute duration if the wipe was able to wipe the maximum surface area multiple times during the duration. "Surface area (in$^2$) w/ one touch" is the total surface area in square inches that one wipe was able keep completely wet for a 2 minute duration with one touch of the wipe.

TABLE 1

Surface coverage of pre-saturated disinfecting disposable wipes

| Sample | Cloth Dimension | Substrate Weight (g/m$^2$) | Substrate Material | Weight Ratio Formula: Substrate | Surface area (in$^2$) w/ multiple touches | Surface area (in$^2$) w/ one touch |
|---|---|---|---|---|---|---|
| Nonwoven Cloth 1 | 6" × 6.75" | 45 | 43/57 PP/cotton | 3.0:1 | 336* | 0* |
| Nonwoven Cloth 2 | 6" × 6.75" | 45 | 43/57 PP/cotton | 3.5:1 | 264 ** | 0** |
| Pre-saturated microfiber wipes | 6.75" × 6.75" | 55 | 100 polyester | 3.5:1 | 1343 ** | 929** |

*keep entire surface complete wet for 3 min
**keep entire surface complete wet for 2 min

EXAMPLES

Example 1

Sample pre-saturated microfiber disinfecting wipes were manufactured in accordance with the present disclosure.

A 55 g/m$^2$ and microfiber cloth manufactured in accordance with the present disclosure and pre-saturated with a QUAT disinfecting formulation was tested against commercially available nonwoven disinfecting wipes containing a QUAT disinfecting formulation. The nonwoven wipes were 6"×6.75" with 45 g/m$^2$ substrate weight. The weight of the microfiber wipes is measured in grams per square meter of material. The nonwoven wipes were a 43%/57% polypropylene/cotton blend. All of the experimental microfiber wipes embodying the present disclosure were 100% polyester (i.e., substrate and microfiber yarn were polyester). The ratio between the weight of the quaternary ammonium chloride based disinfecting formulation to the weight of the dry wipe was also varied. Both 3.5:1 and 4.5:1 ratios for the experimental wipes were tested, whereas the commercially available nonwoven wipes used either 3.0:1 or 3.5:1 ratios. The experimental microfiber cloths, for all weights and all sizes, used a low weight substrate 102 having a first face and an opposed second face, and a microfiber yarn 104 sewn on the low weight substrate 102 in a plurality of parallel rows of straight stitches substantially flush with the first and second faces of the substrate 102. For those experimental microfiber cloths having a substrate weigh of 55 g/m$^2$, the microfiber yarn was formed of 144 microfiber filaments and As can be seen in the results, the pre-saturated disposable disinfecting microfiber wipes were able to keep nearly six times the surface area wet during the multiple-touch test than comparable nonwoven wipes. The nonwoven wipes were only able to keep about 8 times their surface area wet, whereas the experimental microfiber cloths were able to keep more than thirty-five times their area wet for two minutes.

The nonwoven Cloth 1 wipes were unable to keep any surface area completely wet for three minutes during the one-touch test. The nonwoven Cloth 2 wipes were unable to keep any surface area completely wet for two minutes with just one touch. By comparison, an embodiment of the pre-saturated disposable disinfecting microfiber wipes surprisingly was able to keep surface area of at least five times the surface area of the wipe completely wet for two minutes with just one touch.

Example 2

The pre-saturated disposable disinfecting microfiber wipes were also tested for liquid release, tensile strength, and toughness as tested by abrasion, and compared against a commercially available nonwoven pre-saturated wipe. Both a 55 g/m$^2$ and a 70 g/m$^2$ microfiber cloth manufactured in accordance with the present disclosure were tested against the commercially available nonwoven disinfecting wipes. The nonwoven wipes were a 43%/57% polypropylene/cotton blend. The tested embodiments of the microfiber wipes were 100% polyester. For those experimental microfiber cloths having a substrate weigh of 55 g/m², the microfiber yarn was formed of 144 microfiber filaments and had a denier of 75. For those experimental microfiber cloths having a substrate weigh of 70 g/m², the microfiber yarn was formed of 288 microfiber filaments and had a denier of 150.

The liquid release measures the percentage of the disinfecting formulation that was released from the pre-saturated disposable disinfecting wipes onto the surface. The tensile strength of the wipes was tested both parallel and perpendicular to the stitches and reported in lbs. The tensile strength was measured as the maximum force applied to a cloth carried to rupture. The abrasion tests used very fine sandpaper rubbing against the faces of the wipes until a hole was formed in the sample. TABLE 2 displays these results.

TABLE 2

Liquid release, physical properties of disinfectant wipes

| Sample | Construction | Weight (g/m²) | Material | Liquid release (%) | Tensile (lb.) Parallel to stitches direction | Perpendicular to stitches direction | Abrasion (cycles) Dry | Wet |
|---|---|---|---|---|---|---|---|---|
| Nonwoven Cloth 1 | Nonwoven | 45 | 43/57 PP/cotton | 82% | 10.4 | 6.7 | 1 | 6 |
| Experimental Cloth | Microfiber | 70 | 100 polyester | 96% | 57.9 | 14.3 | 39 | 77 |
| Experimental Cloth | Microfiber | 55 | 100 polyester | 98% | 34.9 | 15.9 | 21 | 55 |

As can be seen in the results, both tested experimental embodiments of the pre-saturated disposable disinfecting wipes outperformed the nonwoven wipes in liquid release. The nonwoven wipes were unable to release above 90% of the disinfecting formulation, but the experimental embodiments tested were able to release over 95% of the disinfecting formulation.

Both tested experimental embodiments of the pre-saturated disposable disinfecting wipes beat out the nonwoven wipes in terms of both strength applied parallel to the stitches and strength applied perpendicular to the stitches. The microfiber wipes were 3-5 times stronger lengthwise and more than 2 times as strong widthwise.

Both tested experimental embodiments of the pre-saturated disposable disinfecting wipes stood up substantially stronger to abrasion as well, making the embodiments better for withstanding cleaning, wiping, and disinfecting non-flat surfaces.

While the disclosure has been described with reference to a number of embodiments, it will be understood by those skilled in the art that the disclosure is not limited to such disclosed embodiments. Rather, the disclosure can be modified to incorporate any number of variations, alterations, substitutions, or equivalent arrangements not described herein, but which are commensurate with the spirit and scope of the disclosure. Conditional language used herein, such as "can," "could," "might," or "may," unless specifically stated otherwise, or otherwise understood within the context as used, generally is intended to convey that certain embodiments include, while other embodiments do not include, certain features, elements or functional capabilities. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

What is claimed is:

1. A pre-saturated disposable disinfecting wipe, comprising:
    a microfiber cloth comprising:
        a low weight substrate having a first face and an opposed second face; and
        microfiber yarn attached to the low weight substrate in a plurality of parallel rows of stitches; and
    a disinfecting formulation saturated in the microfiber cloth;
    wherein the microfiber yarn comprises between 100 and 200 microfiber filaments and has a denier of between 50 and 100; and
    wherein the plurality of parallel rows of stitches are spaced between 0.5 mm and 3 mm apart.

2. The pre-saturated disposable disinfecting wipe of claim 1, wherein the disinfecting formulation comprises alcohol, quaternary ammonium chloride (QUAT), quaternary ammonium chloride (QUAT) and alcohol, chlorine bleach, citric acid, peroxygens such as hydrogen peroxide, or peracetic acid.

3. The pre-saturated disposable disinfecting wipe of claim 1, wherein the microfiber yarn is attached to the low weight substrate by sewing the microfiber yarn such that the stitches are straight stitches that are substantially flush with the first and second faces of the substrate.

4. The pre-saturated disposable disinfecting wipe of claim 1, wherein the microfiber yarn is attached to the low weight substrate by stitch-bonding the microfiber yarn onto the low weight substrate.

5. The pre-saturated disposable disinfecting wipe of claim 1, wherein the microfiber cloth is formed of a single layer of the low weight substrate and the microfiber yarn.

6. The pre-saturated disposable disinfecting wipe of claim 1, wherein the microfiber cloth has a weight of about 10 g/m² to about 150 g/m².

7. The pre-saturated disposable disinfecting wipe of claim 1, wherein the microfiber cloth has a weight of about 45 g/m² to about 65 g/m².

8. The pre-saturated disposable disinfecting wipe of claim 1, wherein the microfiber cloth is saturated with the disinfecting formulation in an amount between 3.5 times and 4.5 times a dry weight of the microfiber cloth.

9. The pre-saturated disposable disinfecting wipe of claim 1, wherein the pre-saturated disposable wipe displays a tensile strength measured in a direction parallel to the stitches of greater than 30 pounds.

10. The pre-saturated disposable disinfecting wipe of claim 1, wherein the pre-saturated disposable disinfecting wipe displays a tensile strength measured in a direction perpendicular to the stitches of greater than 10 pounds.

11. The pre-saturated disposable disinfecting wipe of claim 1, wherein the pre-saturated disposable disinfecting wipe is effective to keep a surface area completely wet with the disinfecting formulation for more than 3 minutes after a single application of the wipe to the surface area.

12. The pre-saturated disposable disinfecting wipe of claim 1, wherein the pre-saturated disposable disinfecting wipe displays the ability to keep more than 30 times a surface area of the wipe on a surface wet with the disinfecting formulation for more than 3 minutes using multiple applications of the wipe to the surface.

13. The pre-saturated disposable disinfecting wipe of claim 1, wherein the microfiber yarn has a denier of between 65 and 85.

14. The pre-saturated disposable disinfecting wipe of claim 1, wherein the pre-saturated disposable disinfecting wipe has an abrasion resistance of more than 10 cycles.

15. A method of manufacturing a pre-saturated disposable disinfecting wipe, comprising:
   providing a low weight substrate having a first face and an opposed second face;
   attaching a microfiber yarn to the low weight substrate in a plurality of parallel rows of stitches; and
   saturating the microfiber cloth with a disinfecting formulation;
   wherein the microfiber yarn comprises between 100 and 200 microfiber filaments and has a denier of between 50 and 100; and
   wherein the pre-saturated disposable disinfecting wipe comprises 50 to 500 stitches per square inch.

16. The method of claim 15, wherein the attaching comprising sewing the microfiber yarn such that the stitches are straight stitches that are substantially flush with the first and second faces of the substrate.

17. The method of claim 16, wherein the sewing is performed on a multiline sewing machine.

18. The method of claim 15, wherein the attaching comprises stitch-bonding the microfiber yarn onto the low weight substrate.

19. The method of claim 15, wherein the microfiber cloth is saturated with the disinfecting formulation in an amount of between 3.5 times and 4.5 times of a dry weight of the microfiber cloth.

20. The method of claim 15, wherein the microfiber cloth is saturated with the disinfecting formulation in an amount greater than 6.0 times a dry weight of the microfiber cloth.

21. The method of claim 15, wherein the disinfecting formulation comprises alcohol, quaternary ammonium chloride (QUAT), quaternary ammonium chloride (QUAT) and alcohol, chlorine bleach, citric acid, peroxygens such as hydrogen peroxide, or peracetic acid.

22. The method of claim 15, wherein the pre-saturated disposable disinfecting wipe has an abrasion resistance of more than 10 cycles.

* * * * *